United States Patent [19]
Fisher

[11] Patent Number: 5,376,878
[45] Date of Patent: Dec. 27, 1994

[54] MULTIPLE-APERTURE PARTICLE COUNTING SIZING AND DEFORMABILITY-MEASURING APPARATUS

[76] Inventor: Timothy C. Fisher, 753 Santa Barbara St. #3, Pasadena, Calif. 91101

[21] Appl. No.: 127,412

[22] Filed: Sep. 27, 1993

Related U.S. Application Data

[63] Continuation of Ser. No. 806,033, Dec. 12, 1991, abandoned.

[51] Int. Cl.$^5$ ............................................. G01N 15/07
[52] U.S. Cl. .................. 324/71.4; 422/82.02
[58] Field of Search .................. 422/82.01, 82.02; 324/72.4

[56] References Cited

U.S. PATENT DOCUMENTS

| | | | |
|---|---|---|---|
| 3,811,841 | 5/1974 | Kassel | 324/71.4 |
| 4,438,390 | 4/1984 | Hogg . | |
| 4,926,114 | 5/1990 | Doutre | 324/71.4 |
| 5,023,054 | 6/1991 | Sato | 324/71.4 |

FOREIGN PATENT DOCUMENTS

| | | | |
|---|---|---|---|
| 2145531 | 3/1973 | Germany | 324/71.4 |
| 0179729 | 11/1982 | Japan | 324/71.4 |
| 1456599 | 8/1976 | United Kingdom . | |
| 1602134 | 3/1978 | United Kingdom . | |
| 2163555 | 6/1986 | United Kingdom . | |
| 2232769 | 12/1990 | United Kingdom . | |

*Primary Examiner*—Kenneth A. Wieder
*Assistant Examiner*—Jose M. Solis

[57] ABSTRACT

An apparatus and method for counting and measuring the size of particles, particularly in the range 10 nanometers to 10 micrometers in diameter, and for measuring both the size and deformability of deformable particles, primarily red and white blood cells, in which are provided, in combination: —a membrane 10 containing multiple apertures 12 providing the only means of continuity between two fluid reservoirs 16 and 18; electrodes 20 and 22 mounted one in each reservoir; and another electrode 14 situated inside each aperture, forming part of the wall. The position of electrode 14 effectively divides the aperture into two aperture regions 28 and 30 having similar electrical resistance. In use, a conductive fluid containing the particles is placed into reservoir 16 and aspirated through the apertures into reservoir 18. A voltage $V_{in}$ applied between electrodes 20 and 22, causes a corresponding voltage $V_{out}$ at each electrode 14. Particles entering an aperture increase the resistance of first one aperture portion and then the other, producing a biphasic fluctuation in $V_{out}$, the magnitude of which indicates the particle size. If one of the aperture portions 28 is made smaller than a deformable particle, e.g. a red blood cell, then the duration of the corresponding phase of the signal reflects the deformability of the cell, while the cell size is given by the magnitude of the other phase. The physical and electrical independence of the multiple apertures permits high data acquisition rates, sophisticated noise reduction, and other significant advantages which facilitate the measurement of very small particles.

20 Claims, 4 Drawing Sheets

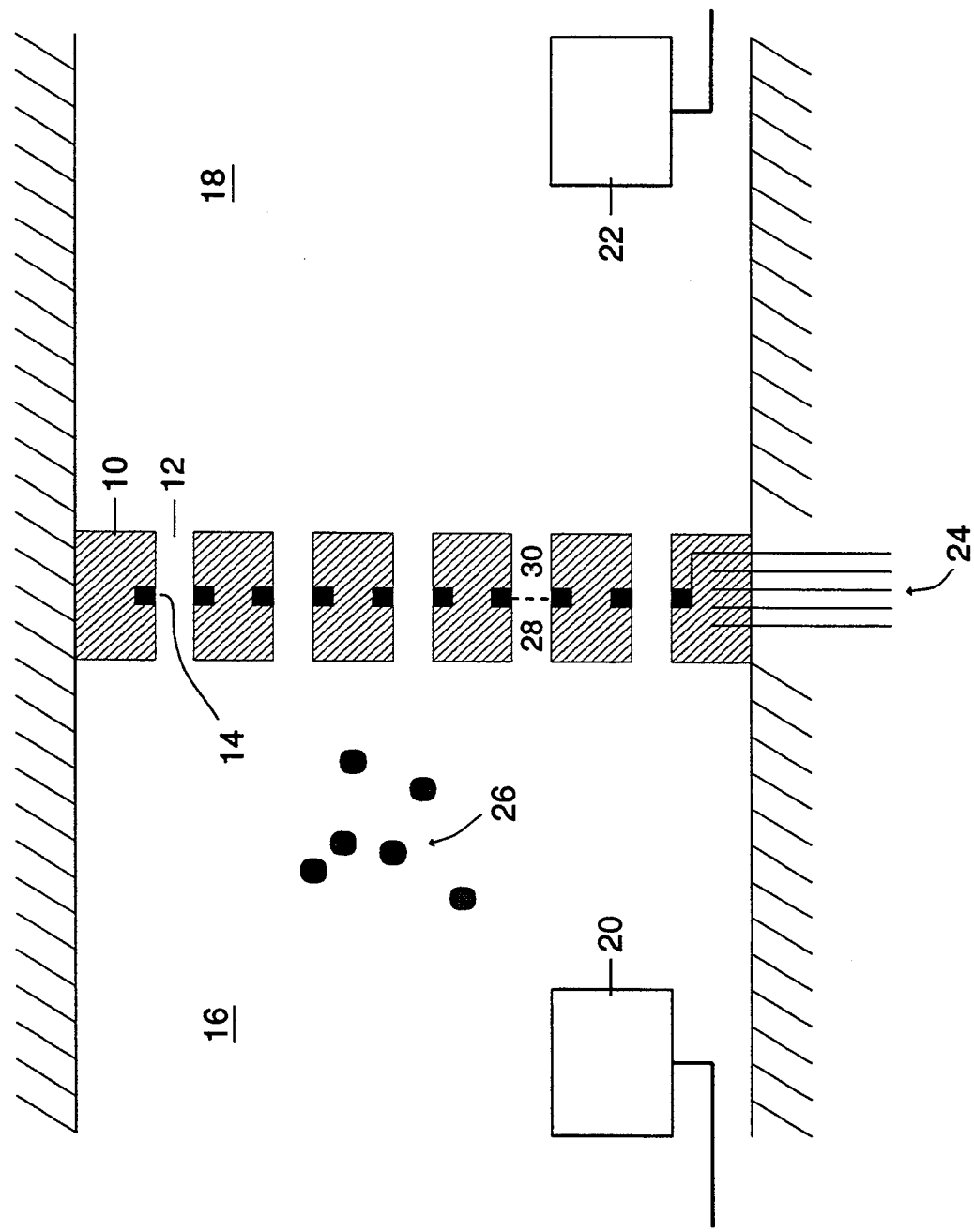
Figure 1)

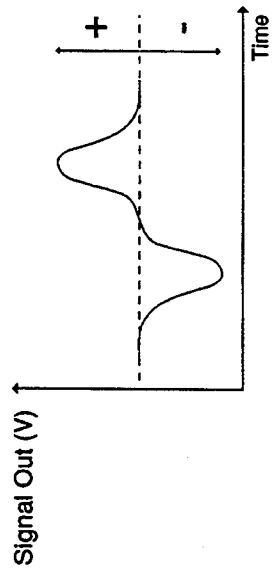
Figure 2)
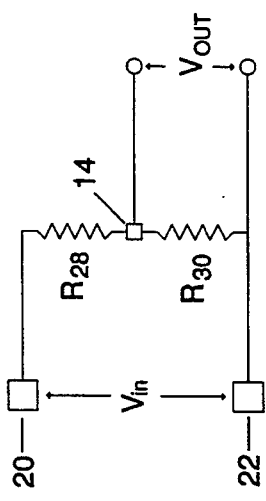
Figure 3)
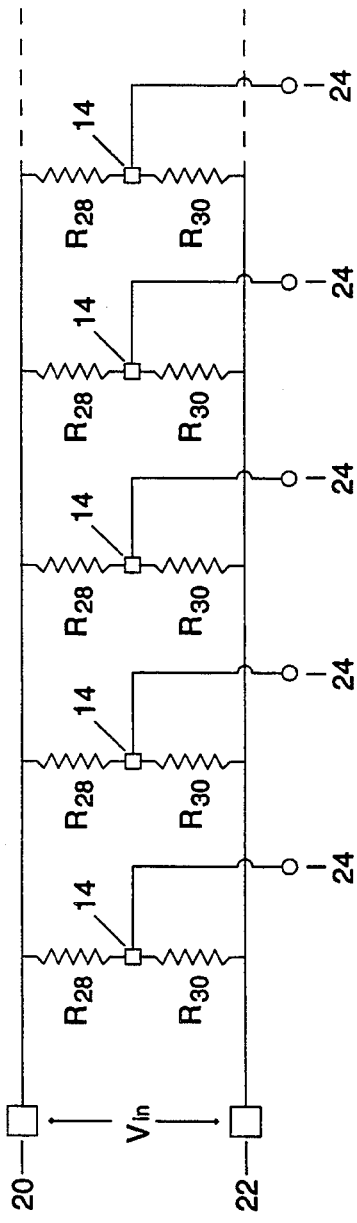
Figure 4)

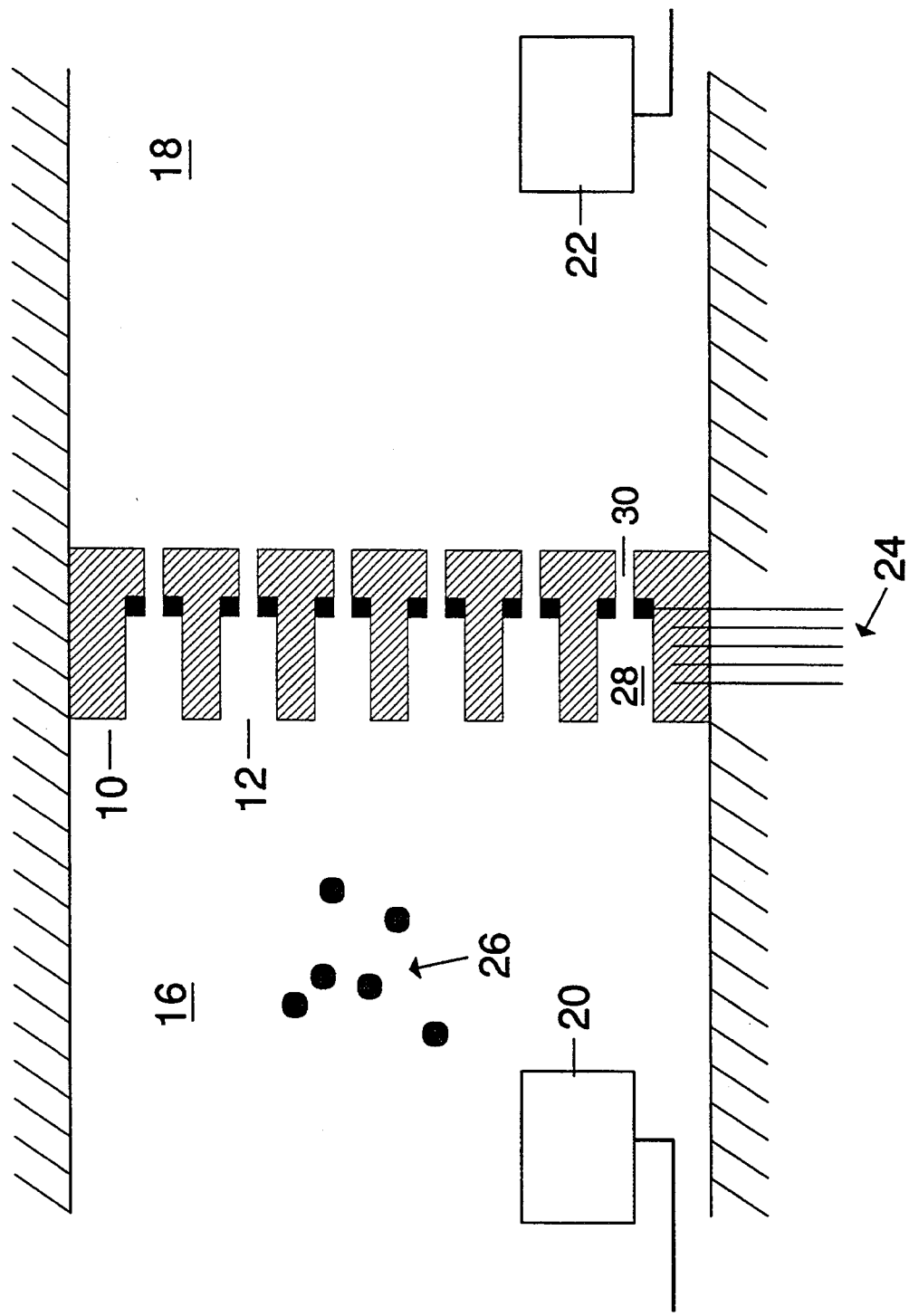
Figure 5)

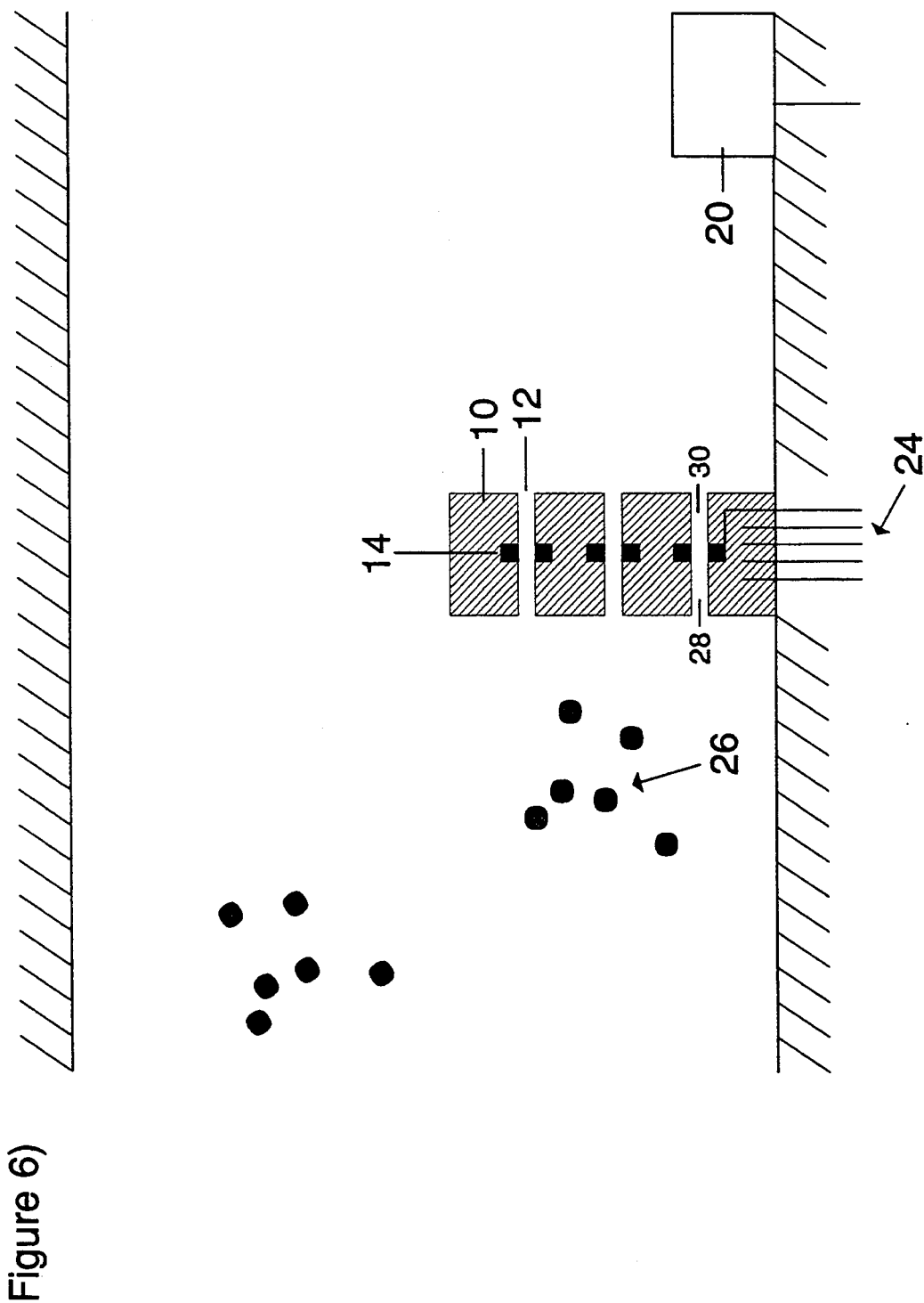

MULTIPLE-APERTURE PARTICLE COUNTING SIZING AND DEFORMABILITY-MEASURING APPARATUS

This is a continuation of application Ser. No. 07/806,033 filed Dec. 12, 1991, now abandoned.

BACKGROUND—FIELD OF THE INVENTION

This invention relates to an apparatus and method to accurately measure the size, number and deformability of particles suspended in a fluid, particularly in the size range from 10 nanometers to 10 micrometers in diameter and including blood cells, based upon the aperture impedance principle.

BACKGROUND—RELATED APPLICATIONS

A patent application relevant to the present application was filed at the British Patent Office on Jun. 13, 1989 (Number 8913593.3) and was published by the British Patent Office on Dec. 13, 1990.

BACKGROUND AND PRIOR ART

Particle Size Measurement

The aperture impedance principle for counting and sizing particles was disclosed in W. H. Coulter U.S. Pat. No. 2,656,508 in 1949. This patent discloses a principle for the measurement of particles suspended in an electrically-conductive fluid. The fluid containing the particles in dilute suspension is aspirated from one electrically-insulating vessel into another similar vessel through a small aperture. This aperture provides the only path for fluid or electrical communication between the two vessels. Electrodes are immersed in the fluid, one in each vessel. The passage of a particle through the aperture causes a brief change in electrical resistance measured between the two electrodes. The magnitude of the transient resistance change (called a "resistive pulse") is a measure of the size of the particle. Several thousand particles may be measured in a few seconds, and the data are usually sorted into classes to provide a distribution histogram showing the number of particles falling into each size range. This principle has subsequently been extended and refined, and is usually referred to as the "aperture impedance" or the "Coulter" principle.

Measurement of particle size in the sub-micrometer range is critical for the production of a wide range of products, for example ceramics, toners, dyes, powders, photographic materials and a large many others. Variation in particle size can critically influence both manufacturing processes and the characteristics of the final product. Sub-micrometer-sized particles are also of critical importance as contaminants in semiconductor manufacturing processes. Currently, automated techniques for the measurement of particles in the sub-micrometer size range fall into two main categories;

a) Laser techniques, in which either the light scattering or the effect of the particles' brownian motion is analyzed to give an estimate of the mean particle volume. Analyses take only a few minutes, but while the mean particle volume is usually accurate, the distribution of particle sizes within the sample cannot be measured precisely.

b) Centrifugal or other elutriation techniques, which physically separate the sample into fractions based on particle size. The number of particles, or the proportion of the original sample, found in each fraction are then estimated by other means. These methods give accurate particle size distribution with reasonable resolution, but they are very slow—up to 30 minutes per sample, which limits their usefulness to laboratory or off-line applications.

Compared to the aperture impedance principle, both of the techniques described above are relatively slow and give lower resolution. The equipment is substantially more expensive and complex. It is therefore of particular advantage to extend the aperture impedance principle to the measurement of particles in this size range. However, although there have been previous attempts, none has been entirely successful due to problems arising from the small apertures required:

For accurate sizing, the diameter of the particle to be measured must lie between approximately 2% to 60% of the aperture diameter. Thus to measure small particles, small apertures are necessary. The smallest apertures commonly in use are about 15 micrometers in diameter, consequently the smallest particles that can be resolved using standard equipment is currently around 0.3 micrometers. Some specialized equipment uses a single sub-micrometer aperture to measure the size and electrophoretic mobility of particles down to 60 nanometers in diameter (DeBlois, Bean and Wesley, Journal of Colloid Science 1977, 61 (2) pp. 323-335). The main difficulties encountered when attempting to measure small particles with these existing aperture impedance techniques are:

a) the small resistive pulse signal generated by small particles is compromised by electrical and acoustic noise. This is the reason for the lower limit of 2% of the aperture diameter for the apertures currently in general use. With yet smaller apertures, such as a sub-micrometer aperture, the lower limit is much higher Than 2% because, while the resistance change depends only on the relative dimensions of the particle and the aperture, the noise floor rises substantially.

b) repeated blockage of the aperture by over-sized particles, aggregates of particles or debris. This affects apertures of all sizes, but becomes a severe problem with small apertures sizes.

Deformability Measurement

Abnormal red blood cell deformability has been described in several diseases, for example sickle cell anemia, malaria and diabetes. In sickle cell anemia, the changes in deformability are of abrupt onset, with the red blood cells changing to a characteristic rigid "sickle" shaped appearance. In this condition they block blood flow in the body tissues, causing extreme pain and tissue damage which may be severe. In contrast, the deformability changes in diabetes are less dramatic, but of a chronic nature. The debilitating complications of diabetes; blindness and kidney failure, result from progressive damage to the smallest blood vessels, and it is believed that the impairment of blood flow through these vessels due to the abnormally rigid red blood cells may contribute to this process.

A device to accurately quantify both subtle and gross changes in red blood cell deformability would therefore have great value both as a research tool and for clinical use. Many different techniques have been developed for this purpose, for example the measurement of the (mechanical) resistance to filtration of diluted blood cell suspensions through membranes containing thousands of microscopic pores typically 3-5 micrometers in diameter. However, no current method is entirely satisfactory, including the most recently developed modification of the filtration technique due to Hanss, Guillet and Vassaux (GB 2, 163,555 A) 1984. This patent discloses an improved apparatus and process for determining red blood cell deformability. The apparatus is similar to the usual aperture impedance apparatus, and uses an insulating membrane filter containing between 15 and 100 pores, each having a diameter of 3 to 5 micrometers, in place of the usual single aperture. Red blood cells have a diameter of 7–8 micrometers and therefore must be deformed as they are aspirated through the pores. As in the aperture impedance particle sizing device, the resistance change across the membrane is measured by electrodes immersed in the fluid on each side of the membrane. However, in this case it is the duration of the resistive pulse that is of interest, rather than the magnitude. The pulse duration indicates the time taken for cells to pass though the pore (the "transit time"). In pathological blood samples the cells deform with more difficulty, and consequently show longer transit times than normal cells. Sub-populations of rigid cells may also be distinguished from a majority of normally deformable cells by their different transit times. However, although it is certainly the best device of its kind currently available, this device suffers from some significant deficiencies:

a) Coincident or nearly-coincident passage of two or more cells through different pores gives rise to a spurious value for the transit time—therefore the cell suspension must be made very dilute to ensure that this is a rare event, but this maneuver compromises the rate at which data can be acquired.

b) Cells which completely block a pore (which is a common event with pathological blood samples), are not detected at all because no resistive pulse occurs—just an increase in the baseline resistance. Also rigid cells having very long transit times are not measured accurately in most cases because another cell is likely to enter another pore before the resistive pulse is completed (i.e. before the rigid cell has left the pore), and although both cells may eventually pass, and the falling edge of both pulses may then be detected, it cannot be determined to which cell each falling edge corresponds.

c) The pores are made by a process which does not guarantee that each has exactly the same diameter. Thus the transit times even of identically-deformable cells may differ if they passed through different pores.

d) The device cannot be used to accurately measure particle size because the multiple pores compromise the signal to noise ratio: In the case that 100 pores are present in the device, the resistance change detected between the two electrodes due to a particle passage in one of these pores is attenuated by a factor of 1000 relative to the sum of the noise, which arises from each pore simultaneously.

OBJECTS OF PRESENT INVENTION

A primary object of the present invention is to provide a device and a method, based upon the known aperture impedance technique, but using a plurality of physically and electrically-independent apertures, which can be used to measure and count particles, particularly in the 10 nanometer to 10 micrometer size range, and which is;

a) rapid and simple in operation;

b) capable of accurate and high resolution particle size measurement;

c) relatively immune from noise, both electrical and acoustic;

d) possessed of a high degree of immunity from the effects of multiple aperture occlusion, this object to be achieved due to the redundancy introduced by the incorporation of a large number of functionally identical apertures into the device.

Another object of the present invention is to provide a device and a method, similar to that described in the previous paragraph, for measuring the size and deformability of particles, particularly (but not limited to) red blood cells and also white blood cells, with the following advantages:

a) Coincident entry of cells into two or more apertures will not result in error in the measured transit time, thus more-concentrated cell suspensions may be used, with a consequent improvement in the data acquisition rate.

b) Every cell in the suspension that enters an aperture will be measured. Cells having long transit times will not be missed, and will have an appropriate transit time recorded, while even those that do not pass through will still be detected.

c) Different-sized apertures may be used simultaneously for a single analysis, because the output from each aperture is detected separately, and each aperture may be calibrated independently.

Still further objects and advantages will become apparent from a consideration of the ensuing description and drawings.

SUMMARY OF INVENTION

The present invention provides an apparatus for counting particles and determining their size and, if desired, their deformability, comprising:

—a membrane having a first reservoir on one side thereof containing a first electrode, and a second reservoir on the other side thereof containing a second electrode —the membrane having a plurality of separate apertures which provide the only means for establishing electrical continuity between the first and second electrodes via electrically conductive fluid contained in the reservoirs, each aperture comprising a first portion leading into a second portion, and;

—a third electrode, located at the junction of the first and second portions, which is contained entirely within each aperture, and which forms part of the wall of each aperture, in use the changes in electrical resistance between the third and first electrodes or between the third and second electrodes being indicative of the presence of a particle within the aperture, the size of the particle and its transit time within the aperture.

As used herein, the term "membrane" is intended to mean a thin sheet of electrically-insulating material, either rigid or flexible, or a composite sandwich of two or more such materials. The term particle is to be interpreted to include not only rigid particles, but also deformable particles, composed of both inorganic or organic matter, and also to include biological particles and living cells.

The purpose of the first and second portions of the aperture, with the third electrode positioned at the junction of these portions, is to create a significant electrical resistance between the first and third electrodes and also between the second and third electrodes. The electrical path between the third electrodes and the electrodes in the reservoirs may be considered to consist of two parts: 1) the conductive fluid contained within the corresponding portion of the aperture, the resistance of which predominates, and 2) the fluid situated between the electrode contained in the reservoir and the entrance of the aperture, i.e. the surface of the membrane, which contributes very little to the total resistance between the electrodes, is due to the huge cross-sectional area of the fluid paths in the large reservoirs compared to that in the tiny apertures. The apparatus will be always be configured such that the resistance of the fluid in the reservoirs is absolutely insignificant compared to the resistance of the apertures. Generally the electrical resistances each aperture portion will be arranged to be approximately equal, but this is not essential.

The particles to be measured will normally have a much lower electrical conductivity than the suspending fluid. When a particle enters the first aperture portion, the electrical resistance between the first and third electrode increases. If a known voltage is applied between the first and second electrodes, then this resistance change will vary the voltage detected at the third electrode. Continued passage of the particle into the second aperture portion increases the electrical resistance between the third and second electrodes so varying again the voltage detected at the third electrode, but in the opposite sense. It is of particular significance that the change in resistance occurring in any one aperture due to the passage of a particle therethrough will have negligible influence on any other aperture, thus all apertures are not only physically, but also electrically independent of any other.

For most applications, the number of apertures in the membrane is in the region 10 to 100. Because each aperture is physically and electrically independent, the maximum number of apertures is limited only by the practical considerations of making electrical connections to all the third electrodes and analyzing all the resulting signals in a reasonable time period. Thus a membrane with thousands of apertures is feasible. In fact, it is not necessary to use all of the apertures at one time—any number may be left unconnected. Similarly, apertures may be disconnected or ignored should they become blocked, or substituted by a "reserve" aperture which was previously left unused.

Generally, the same electrically-conductive fluid will be placed in both reservoirs. For the analysis of biological cells or other sensitive material, this solution will be such as to maintain the cells intact and substantially unchanged.

The invention also relates to a corresponding method for counting particles and for measuring their size and, if desired, their deformability, in which;
— a suspension of the particles or cells in a suitable conducting fluid is placed in one or other of the reservoirs, with similar or identical fluid, usually but not necessarily particle-free, placed in the other;
— a pressure difference is applied across the membrane to induce flow of the fluid containing the particles or cells into and through the apertures, the pressure being dependent on the application, but typically in the range of 0.1 to 30 centimeters of water;
— the electrical potentials sensed at the third electrodes are fed into a high input impedance amplifier and thence to a signal processing device programmed to extract relevant parameters according to the particular application, and to convert these into the number and size of particles, and if appropriate, their deformability.

An embodiment of the present invention will now be described, by way of example only, with reference to the accompanying drawings.

DRAWINGS

FIG. 1 shows a schematic cross-sectional view of the apparatus, the section passing through five identical apertures in the membrane;

FIG. 2 represents an electrical circuit which is electrically equivalent to a single aperture containing the conductive fluid;

FIG. 3 indicates the change in electrical voltage measured between the third electrode and either the first or second electrode as a particle passes through the aperture. This represents a typical output from a single aperture having uniform diameter over its entire length.

FIG. 4 shows a combination of five copies of the circuit illustrated in FIG. 2, the whole forming an electrically equivalent circuit to the five aperture apparatus of FIG. 1.

FIG. 5 indicates a preferred embodiment of the invention for the purpose of measuring blood cell size and deformability.

FIG. 6 indicates a preferred embodiment of the invention for the purpose of operation within a single vessel, and which does not require separate reservoirs on each side of the membrane.

REFERENCE NUMERALS IN DRAWINGS 10 membrane
12 aperture in membrane (10)
14 'third' electrode contained within aperture
16 reservoir A containing the conductive fluid
18 reservoir B containing the conductive fluid
20 'first' electrode
22 'second' electrode
24 multiple electrically-conductive tracks leading from electrode (14) in each aperture
26 particles suspended in the conductive fluid
28 'first' aperture portion
30 'second' aperture portion Throughout the figures of the drawings the same parts are designated by the same reference numerals.

DETAILED DESCRIPTION OF THE PREFERRED EMBODIMENT

FIG. 1 shows a schematic cross section of the device in the vicinity of the electrically-insulating membrane 10. Membrane 10 is situated between two reservoirs 16,18, containing electrodes 20, 22, which are termed the 'first' electrode 20 and the 'second' electrode 22. Membrane 10 may be formed of a single sheet or a composite sandwich of two or more sheets of the same or different materials. Five identical cylindrical apertures 12, are illustrated, containing in their walls a 'third' electrode 14. For the purposes of labelling the electrical schematics FIGS. 2 and 4, the position of electrode 14 is considered to subdivide the aperture into a 'first' portion 28 and a 'second' portion 30. Many more apertures 12 would usually be present in membrane 10, but have been omitted for the sake of clarity. Also for reasons of clarity, reservoirs 16 and 18, on each side of the membrane, are not shown in their entirety, but they should be considered to represent complete vessels capable of containing an electrically conductive fluid, and capable of withstanding a pressure difference across membrane 10 sufficient to propel the fluid from one reservoir (16 or 18) to the other through the apertures 12. Each electrode 14 is associated with an output lead 24 embedded within the body of the membrane 10 and therefore insulated from the conductive fluid. These leads 24 convey the signal to the outside of the device, where they are connected to suitable apparatus for analysis. The only electrical connection between reservoirs 16 and 18 is through the apertures (12). Suspended particles 26 are also illustrated, for completeness. The dimensions of the apertures (12) will vary greatly with the intended application, but for the analysis of submicron particles might typically lie in the range 0.5 to 5 micrometers in diameter by 10 to 100 micrometers in length.

FIG. 2 shows an electrically circuit equivalent to a single aperture 12 filled with the conductive fluid. R28 signifies a resistance equivalent to that of the 'first' aperture portion 28, while R30 represents the resistance of the 'second' aperture portion 30. Thus the total single aperture resistance would be given by R28+R30, which, because the resistance of the fluid in reservoirs 16,18 is negligible, also represents the resistance between electrodes 20 and 22 due to a single aperture. In use a suitable voltage $V_{in}$ is applied between electrodes 20 and 22. The resistances of each aperture portion R28 and R30 are generally arranged to be similar, such that $V_{out}$ is approximately one-half of $V_{in}$, although this is not an essential feature. FIG. 3 shows the typical form of the voltage change at electrode 14 detected during the passage of a particle through a single aperture.

FIG. 4 shows the equivalent electrical circuit for the five apertures shown in FIG. 1. It can be seen that, so long as the voltage applied between electrodes 20 and 22 is maintained constant, any change in R28 or R30 in an aperture portion due to the passage of a particle will only vary the voltage at that particular aperture's corresponding 'third' electrode 14, and will have no influence whatsoever on any other aperture or electrode.

FIG. 5 shows a modification of the device to facilitate blood cell size and deformability measurement. In this example aperture portion 28 is enlarged relative to aperture portion 30. Typical dimensions for the two portions would be 50 micrometers in diameter for 28 and 5 micrometers in diameter for 30. The length of the larger portion is typically significantly extended to make the cross-sectional area-to-length ratio, and consequently the resistance, similar in both aperture portions 28 and 30. Another advantageous configuration of the device is indicated in FIG. 6. In this example there is no requirement for separate reservoirs; membrane 10 may be immersed in any single vessel or contained within a pipe so long as some means is provided to propel the suspending fluid and particles 26 through apertures 12, perhaps simply the main fluid flow in the pipe, as indicated. Only one electrode 20 external to the membrane is required, and it is the change in resistance measured between the internal electrode 14 within the aperture and the external electrode 20 that is used to determine the particle size.

There are several possible methods to produce the membranes. In the most simple large scale prototype, holes were drilled through a sandwich of gold foil tracks mounted in epoxy resin between two thin sheets of glass, using a small (0.5 millimeter) diamond drill. However, such techniques cannot be used to produce the very small apertures requred for sub-micron size measurement. One means to form membranes having suitably-sized apertures is to prepare electrodes 14 and leads 24 on the surface of a thin glass sheet by electron beam lithography, to lay over these a coating of an etchable polymer, for example polyamide, through which the first portion of the pores is made (again by electron beam lithography) and finally to etch connecting channels through the glass sheet to form the second portion.

In a particularly advantageous embodiment, the device may be produced by a combination of photo or electron-beam lithography and ion-beam machining in a substrate suitable for the manufacture of semiconductor devices, for example silicon, followed by the deposition of an inert insulating layer of a suitable substance, for example silicon dioxide. In this case the conductive tracks 24 and electrodes 14 can be made by techniques similar to those used in the manufacture of integrated circuits. An advantage of this method of production is that active semiconductor circuitry such as amplifiers and logic gates may be placed directly on the device to perform some pre-processing of the signal. In particular, high-input impedance amplifiers placed in close proximity to the pore electrodes would minimize the current drawn from these electrodes and consequently reduce the risk of polarization.

OPERATION

In use, an appropriate voltage, for example 5 volts, is applied between electrodes 20 and 22 as described above. A suspension of the particles to be analyzed is introduced into reservoir 16, and is aspirated through the apertures 12 under a pressure of between 0.1 and 30 centimeters of water, for example 5 centimeters of water, into reservoir 18. Particles pass through with the fluid and (because they have a lower conductivity than the conductive fluid) cause an increase in the resistance of the aperture which is detected by electrode 14. The precise form of the apparatus and also of the resulting output signal depends upon the application as follows:

a) If the number and size of small particles is to be determined, the aperture size used is chosen with regard to the expected size range of the particles, such that the majority of particles lie within 2% to 60% of the aperture diameter. Apertures of a the form illustrated in FIG. 1, having a constant diameter throughout both aperture portions 28 and 30, are appropriate for this type of analysis. The aspirated particles generate a pulse (detected as a change in the $V_{out}$ at electrode 14) as they enter each pore region, of equal magnitude but opposite sign as illustrated in FIG. 3. The simple occurrence of the voltage change allows the number of particles to be easily counted, while the size is derived from the magnitude of the voltage change. For this application, the particles might also be propelled through the apertures by electrophoretic or electroosmotic potentials instead, or in addition to, the trans-membrane pressure difference. The additional information gained in this manner, when combined with the size measurement, would be of value in the study of colloids.

b) if the size and deformability of particles (usually, though not necessarily red or white blood cells) is to be determined, then apparatus according to the description of FIG. 5 is used, having one large aperture portion 28, up to 10 times the diameter of the particles, and one small portion 30 that is actually narrower than the particles, for example 5 micrometers in diameter. It is the presence of this aperture section smaller than the particles that is the key to the deformability measurement. Particles or blood cells propelled through the apertures first enter the larger portion 28, where the magnitude of the resistance change indicates the cell's size. The cell then approaches the smaller portion 30 but cannot pass easily because it has a larger diameter (7-8 micrometers for a red blood cell). Eventually the cell deforms sufficiently to pass through, giving a resistive pulse of long duration from which the transit time of the cell, and hence its deformability, can be measured.

c) Because the device is arranged to provide a significant electrical resistance between the internal electrode 14 and the surrounding fluid on each side of the aperture, it is possible to operate the device with a single external electrode in a single reservoir, with the device configured as indicated in FIG. 6. This embodiment can be used in inaccessible places such as within pipes or process vessels, to monitor samples on-line and remotely, and in any situation where the suspending fluid cannot be divided into two electrically separated portions. The single electrode could also, under appropriate circumstances, be replaced by the vessel or pipe itself, further simplifying the apparatus. Particles passing through the aperture will generate resistance changes in the same manner as described above, though the output will be bimodal or even unimodal in this case rather than biphasic. However, in order to measure the resistance change in the aperture it is necessary for significant currents to flow from the internal electrode 14, and careful precautions must be taken to avoid polarization of this small electrode, for example by using a high frequency AC voltage rather than DC as indicated in the previous examples (though in principle AC could be used in all cases).

ADVANTAGES OF THE CURRENT INVENTION

The fundamental advantage of this invention arises from the physical and electrical independence of the apertures, which allows any number of apertures to be operated in parallel. The simultaneous use of multiple apertures provides many advantages:

a) Rapid data acquisition rate. The rate of particle analysis with standard single aperture systems is limited by the need to maintain the particle concentration at a level where the coincident entry of more than one particle into the aperture is a rare event. With the present invention, the maximum single-aperture data acquisition rate is simply multiplied by the number of apertures in operation, for example by 100 times if that many apertures are available. Thus particle concentrations significantly below the coincidence threshold can be analyzed extremely rapidly. It also permits the analysis of samples having extremely low particle concentrations without pre-processing.

The next two advantages are particularly valuable with regard to the measurement of particles in the submicron size range:

b) Virtual immunity from aperture occlusion: Devices with single apertures, especially small apertures, are frustrating to operate because of their susceptibility to repeated blockage by over-large particles or debris. In the present invention, the large number of independent apertures provides a high degree of redundancy; thus the occlusion of many apertures may be tolerated before the operation must be abandoned and the apertures cleared.

c) Elegant techniques for noise reduction are available due to the multiplicity of apertures and their particular construction: Noise arising from both extrinsic sources (for example, electromagnetic interference and vibration) and intrinsic sources (for example, the Johnson effect, other types of resistor noise, and the coincident entry of particles into a single aperture) may be actively suppressed as follows:

i) In the case of extrinsic noise, the apertures (which are arranged to be physically close together), will pick up the noise in a similar manner. If, while a particle measurement is made in one aperture, noise is detected in the adjacent apertures, the potentially corrupted data can be rejected. Alternatively, under such circumstances, valid signals can be extracted from the noise by the subtraction of a baseline signal derived from the adjacent (unoccupied) apertures.

ii) Intrinsic noise due to the Johnson effect (thermal noise due to random motion of charge carriers within the conductive fluid) and other types or 'resistor' noise, are the most significant factors in determining the lower limit of particle sizing with the aperture impedance technique. The current invention provides two quite distinct ways to minimize this noise and hence improve the signal to nose ratio for small particles. The first arises out of the fact that coincidence will inherently be much lower when using multiple apertures because of the low particle concentrations that can be employed while maintaining an acceptable data acquisition rate. Reduced coincidence permits the use of apertures having a very high aspect ratio (length-to-diameter ratio) which improves both the signal-to-noise ratio and the resolution of the measurement: the resistive pulses arising from long apertures have a long duration, up to several milliseconds. The noise, which is mostly of much higher frequency than the pulse, can be easily eliminated using a very low-pass filter without compromising the particle size information contained in the pulse height. The second way to minimize the intrinsic noise is to examine the shape of the (normally biphasic) output signal. A mismatch between the shape or amplitude of the positive and negative phases for each particle passage, or an incorrect time relationship between the two phases indicates a spurious event, such as coincidence or a noise spike, and the pulse is rejected. Finally, by inverting and reversing the negative phase of the pulse, the two phases may be averaged, again reducing the noise.

d) The ability to use apertures of different sizes, or even shapes, on the same device: This is possible because of the independent operation of the apertures. There are two main considerations here: Firstly unwanted variation in the size of the pores may be corrected for on an individual basis (i.e. each pore may be calibrated) by measuring a a suspension standard reference particles of known dimensions. The corrections would be applied to the output by the data analysis system after the fact. Secondly, for the purposes of blood cell deformability analysis it may be considered advantageous to measure the transit time of the cells through a range of different apertures, because different defects become most evident at different degrees of deformation.

The further advantages e and f are specific to the particular application:

e) When used for blood cell deformability and size measurement—the ability to simultaneously measure both the transit time and the size of each cell, using the device as illustrated in FIG. 5. It is well known that transit time is related to particle size, but it has not previously been possible to measure both these parameters simultaneously on individual cells.

f) When used for particle size analysis—the ability to use the device for on-line (or in-line) or remote monitoring. The aperture redundancy is a particular advantage for this application, as it will permit unattended operation for longer periods than would be expected for a single aperture device.

SUMMARY

Thus the current invention extends the known aperture impedance method to provide an advantageous means to count and measure the size and, if desired, the deformability of particles in the micrometer and nanometer size range. While the foregoing description contains many specificities, these should not be construed as limitations on the scope of the invention, but rather as an example of some preferred embodiments thereof. Other variations are possible, for example the placement of additional electrodes at intervals within the aperture, which would further enhance the signal-to-noise ratio; the resulting multi-phasic resistive pulse being combined to generate a single averaged pulse.

I claim:

1. An apparatus for analyzing particles, which comprises:
   a) a sheet of material having a first reservoir on one side thereof containing a first electrode and a second reservoir on the other side thereof containing a second electrode;
   b) said sheet of material having a plurality of apertures therethrough, which provide in use the only electrical continuity between said first electrode and said second electrode via electrically conductive liquid contained in said reservoirs, each aperture comprising a first portion leading into a second portion;
   c) means to cause the movement of said electrically conductive liquid through said apertures;
   d) means to provide a reference electrical potential difference between said first and said second electrodes;
   e) a respective third electrode located at the junction of said first aperture portion and said second aperture portion in each of said apertures, in use the changes in electrical potential sensed at said third electrode being indicative of the presence of a particle within said aperture, the size of said particle, and the transit time of said particle within each of said aperture portions;

whereby said changes in electrical potential due to the passage of a particle through any one of said apertures are unaffected by the simultaneous passage of another particle through any other aperture and said changes in electrical potential indicate which aperture each particle has passed through, thus providing the ability to independently calibrate each aperture and facilitating the simultaneous detection and accurate measurement of multiple particles.

2. An apparatus according to claim 1, wherein each of said apertures comprises two said aperture portions of identical length and diameter.

3. An apparatus according to claim 1, wherein said apertures have a smaller diameter than the particles to be measured, whereby said changes in electrical potential sensed at said third electrodes indicates the time taken for a deformable particle to deform sufficiently to pass through said apertures.

4. An apparatus according to claim 1, wherein one of said aperture portions has a smaller diameter than the particles to be measured, whereby the duration of said changes in electrical potential sensed at said third electrode indicates the time taken for a deformable particle to deform sufficiently to pass through said small diameter aperture portion, while the magnitude of said changes in electrical potential sensed as said particle passes through the larger portion of said aperture indicates the size of said particle.

5. An apparatus according to claim 1, fabricated such that a proportion of said apertures have a different diameter to the remaining apertures.

6. An apparatus according to claim 1, fabricated such that a proportion of said apertures have different cross-sectional shapes in the plane of said sheet of material than the remaining apertures.

7. An apparatus according to claim 1, wherein a plurality of additional electrodes, each of identical form to, but physically and electrically distinct from, said third electrodes, are located within each of said apertures, the changes in electrical potential detected at each of said additional electrodes and said third electrode being combined in order to improve the precision of the particle measurement.

8. Apparatus comprising:
   a) a sheet of material having a first reservoir on one side thereof, and a second reservoir on the other side thereof, each of said reservoirs containing an electrically-conductive liquid;
   b) a first electrode immersed in said electrically-conductive liquid in said first reservoir, and a second electrode immersed in said second reservoir;
   c) said sheet of material having a plurality of apertures therethrough, which provide in use the only path between said first and said second reservoirs for the passage of electrical current, for the passage of said electrically-conductive fluid, and for the passage of particulate material suspended within said electrically conductive fluid;
   d) means to cause the flow of said fluid through said apertures;
   e) means to provide a reference electrical potential difference between said first and second electrodes;
   f) a respective third electrode located within each of said apertures, said third electrode being located at a significant distance from each open end of said aperture, the position of said third electrode subdividing said aperture into two separate sensing zones;

in use the changes in electrical potential sensed at said third electrode being indicative of the presence of a particle within said aperture, the size of said particle, and the time taken for said particle to travel from the entrance to the exit of said aperture in the direction of flow of said fluid;

whereby said changes in electrical potential due to the passage of a particle through any one of said apertures are unaffected by the simultaneous passage of another particle through any other aperture and said changes in electrical potential indicate which aperture each particle has passed through, thus providing the ability to independently calibrate each aperture and facilitating the simultaneous detection and accurate measurement of multiple particles.

9. An apparatus according to claim 8, wherein each of said two sensing zones within each of said apertures are of identical length and diameter.

10. An apparatus according to claim 8, wherein said apertures have a smaller diameter than the particles to be measured, whereby said changes in electrical potential sensed at said third electrodes records the time taken for a deformable particle to deform sufficiently to pass through said apertures.

11. An apparatus according to claim 8, wherein one of said sensing zones has a smaller diameter than the particles to be measured, whereby the duration of said changes in electrical potential sensed at said third electrode indicates the time taken for a deformable particle to deform sufficiently to pass through said smaller sensing zone, while the magnitude of said changes in electrical potential sensed as said particle passes through said larger sensing zone indicates the size of said particle.

12. An apparatus according to claim 8, fabricated such that a proportion of said apertures have a different diameter to the remaining apertures.

13. An apparatus according to claim 8, fabricated such that a proportion of said apertures have different cross-sectional shapes in the plane of said sheet of material than the remaining apertures.

14. An apparatus according to claim 8, wherein a plurality of additional electrodes, each of identical form to, but physically and electrically distinct from, said third electrodes, are located within each of said apertures, thereby subdividing each aperture into at least three sensing zones the changes in electrical potential detected at each of said additional electrodes and said third electrode being combined in order to improve the precision of the particle measurement.

15. An apparatus for analyzing particles suspended in an electrically conductive fluid, comprising, in combination;

a) a sheet of material having a first reservoir on one side thereof containing a first electrode and a second reservoir on the other side thereof containing a second electrode; said sheet of material having a plurality of apertures therethrough, which provide the only electrical continuity between said first electrode and said second electrode via said electrically-conductive fluid contained in said reservoirs;

b) means to cause said electrically conductive fluid to flow through said apertures;

c) respective third electrodes situated within each of said apertures which make electrical contact with said electrically-conductive fluid, each respective third electrode being electrically and physically distinct from any other;

d) electrical circuitry connected to said first and second electrodes and to each one of said third electrodes, said circuitry being operable in conjunction with said electrodes to apply a reference electrical potential between said first and second electrodes, and to detect changes in electrical potential at each one of said third electrodes, said changes being indicative of the presence of a particle within said aperture, the size of said particle, and the time taken for said particle to pass through each said aperture in the direction of flow of said electrically-conductive fluid;

whereby each of said apertures functions independently and simultaneously as a particle counting and measuring device, said electrical changes detected at any one of said third electrodes during the passage of a particle is independent of simultaneous particle passage events occurring in other apertures, thus providing the ability to independently calibrate each aperture and facilitating the simultaneous detection and accurate measurement of multiple particles.

16. An apparatus according to claim 15, wherein said apertures have a smaller diameter than the particles to be measured, whereby the changes in electrical potential sensed at said third electrodes will record the time taken for a particle to deform sufficiently to pass through said apertures.

17. An apparatus according to claim 15, wherein the diameter of that part of each of said apertures which lies on one side of its respective third electrode differs from that part of said aperture which lies to the other side.

18. An apparatus according to claim 17, wherein one of said parts of said aperture has a smaller diameter than the particles to be measured, whereby the changes in electrical potential sensed at said respective third electrode during the passage of a particle through said smaller part of said aperture indicates the deformation of said particle, while the changes in electrical potential sensed as said particle passes through the larger part of said aperture indicates the size of said particle.

19. An apparatus according to claim 15, wherein some of said apertures have a different cross-sectional diameter, considered in the plane of said sheet of material, than the other apertures.

20. An apparatus according to claim 15, fabricated such that a proportion of said apertures have different cross-sectional shapes in the plane of said sheet of material than the remaining apertures.

* * * * *